(12) United States Patent
Capaldo et al.

(10) Patent No.: US 6,909,502 B2
(45) Date of Patent: Jun. 21, 2005

(54) METHOD AND APPARATUS FOR MEASURING RIPPLE AND DISTORTION IN A TRANSPARENT MATERIAL

(75) Inventors: Kevin Capaldo, Mt Vernon, IN (US); Safwat Tadros, Evansville, IN (US); Charles Vickers, Mt. Vernon, IN (US)

(73) Assignee: General Electric, Pittsfield, MA (US)

( * ) Notice: Subject to any disclaimer, the term of this patent is extended or adjusted under 35 U.S.C. 154(b) by 301 days.

(21) Appl. No.: 10/266,119

(22) Filed: Oct. 7, 2002

(65) Prior Publication Data

US 2003/0151739 A1 Aug. 14, 2003

Related U.S. Application Data

(60) Provisional application No. 60/344,264, filed on Dec. 27, 2001.

(51) Int. Cl.[7] ............................................... G01N 21/88
(52) U.S. Cl. ................................................... 356/239.2
(58) Field of Search .......................... 356/239.1, 239.2, 356/239.7

(56) References Cited

U.S. PATENT DOCUMENTS

| 4,310,242 | A | * | 1/1982 | Genco et al. ................ 356/128 |
| 5,146,282 | A | * | 9/1992 | Guering et al. ........... 356/239.1 |
| 5,175,030 | A |   | 12/1992 | Lu et al. ........................ 428/30 |
| 5,183,597 | A |   | 2/1993 | Lu .............................. 264/1.4 |
| 5,271,968 | A |   | 12/1993 | Coyle et al. ................. 427/558 |
| 5,468,542 | A |   | 11/1995 | Crouch ........................ 428/215 |
| 5,626,800 | A |   | 5/1997 | Williams et al. ........... 264/1.38 |
| 5,691,811 | A |   | 11/1997 | Kihira |
| 5,694,479 | A | * | 12/1997 | Guering et al. ............. 382/141 |
| 5,726,749 | A |   | 3/1998 | Schave ........................ 356/239 |
| 5,812,260 | A |   | 9/1998 | Louisnathan ................ 356/239 |
| 5,880,843 | A |   | 3/1999 | Hermosillo-Valadez et al. ........................... 356/371 |
| 6,011,620 | A |   | 1/2000 | Sites et al. ............... 356/239.1 |
| 6,208,412 | B1 |   | 3/2001 | Ladewski ................ 356/239.1 |
| 6,275,286 | B1 |   | 8/2001 | Hawbold et al. |
| 6,280,063 | B1 |   | 8/2001 | Fong et al. ................. 362/333 |
| 2003/0108710 | A1 |   | 6/2003 | Coyle et al. ............... 428/64.4 |

OTHER PUBLICATIONS

Residual Stress Testing for Transparent Polymers (MDDI archive, Mar. 99)—Alex S. Redner and Barbara Hoffman.
Japanese Patent No. JP2002148142; Publication Date: May 22, 2002; Abstract Only; 1 page.
Japanese Patent No. JP2002365221; Publication Date: Dec. 18, 2002; Abstract Only; 1 page.
ARICHIVES, Nov. 2000, http://www.lasor.com/archives.htm; 7 pages.

* cited by examiner

Primary Examiner—Richard A. Rosenberger

(57) ABSTRACT

An apparatus and method for quantitatively measuring ripple and distortion levels in a transparent sheet (or film) material is provided. The apparatus includes a light source for projecting light beams onto a screen. A frame assembly is positioned intermediate to the light source and is adapted to hold the transparent sheet material at a predetermined angle and distance from the screen. The light beams pass though the transparent sheet material and projects an image onto the screen. The process includes digitally capturing the image and generating parameter signals from the digital image. The parameter signals are used in a model to quantitatively assign a value to the level of ripple and distortion present in the transparent sheet material.

17 Claims, 6 Drawing Sheets

```
The regression equation is
Ripple Quality = - 12.2 + 2.10 sigma vert + 0.761 sigma pxp + 115 (1")
              - 320 (1")^2 + 23.5 (0.3")

Predictor       Coef      StDev        T         P       VIF
Constant      -12.181     1.715     -7.10     0.000
sigma ve        2.0952    0.2747     7.63     0.000      5.3
sigma px        0.7608    0.2432     3.13     0.003      2.8
(1")          115.34     23.00       5.01     0.000     29.4
(1")^2       -319.75     86.25      -3.71     0.001     30.3
(0.3")         23.543     5.849      4.03     0.000      2.0

S = 1.380      R-Sq = 95.3%      R-Sq(adj) = 94.8%

Analysis of Variance

Source        DF         SS         MS         F         P
Regression     5    1592.51     318.50    167.31     0.000
Error         41      78.05       1.90
Total         46    1670.56

Source        DF      Seq SS
sigma ve       1    1488.25
sigma px       1       4.62
(1")           1      35.54
(1")^2         1      33.25
(0.3")         1      30.85

Unusual Observations
Obs   sigma ve   Ripple Q     Fit   StDev Fit   Residual   St Resid
 29      7.62     19.770    21.994     0.926     -2.224    -2.17RX
 30      7.17     26.060    24.928     0.978      1.132     1.16 X
 34      6.40     22.000    21.302     0.906      0.698     0.67 X
 35      8.00     23.000    21.714     1.142      1.286     1.66 X
 38      2.71     10.000     9.266     1.072      0.734     0.84 X R denotes an observation with a large standardized residual
X denotes an observation whose X value gives it large influence.

Durbin-Watson statistic = 1.42

No evidence of lack of fit (P > 0.1)
```

Figure 6

METHOD AND APPARATUS FOR MEASURING RIPPLE AND DISTORTION IN A TRANSPARENT MATERIAL

CROSS-REFERENCE TO RELATED APPLICATIONS

This application is related to and claims priority from Provisional Application No. 60/344,264 filed on Dec. 27, 2001, the entire contents of which are incorporated.

BACKGROUND OF THE INVENTION

This disclosure relates to a process for measuring optical properties in a transparent material and more particularly, to a process for quantitatively measuring ripple and distortion present in the transparent material.

During the manufacture of transparent materials, optical defects and deviations may be produced that render the transparent material optically imperfect. Optical imperfections are of special concern in glass and plastic sheet applications where optical defects are unacceptable from a quality control standpoint. Optical quality defects include inconsistencies in light transmission and/or bending of light that distorts the physical dimensions of the viewed object. Ripples, distortion, gels, scratches, particles, die lines, and grind lines are common categories of optical quality defects.

Ripples are commonly found in transparent materials formed from continuous web processes. Ripples are generally characterized as a periodic distortion wave that orients itself across the web. Ripples may be caused by oscillations in calendaring roll speeds (i.e., gear ripples), release dynamics from the calendaring rolls and other transient oscillations in force (i.e., stick ripples), temperature fluctuations that occur between 0.1 and 100 hertz depending on the line speed, roller bearing inaccuracies, resonance oscillations of the roll or roll stack, motor speed control, bead dynamics, chill marks, pull roll inconsistencies, oscillations from shear, and the like. Ripples may be very sharp and distinct or may be fuzzy at the edges (from distortion) but are generally defined by their consistent cross web orientation.

Distortion also refers to waves. However, the waves presented show less directional orientation than ripples and as such, can be either in the cross web direction or in the machine direction. Distortion in extruded sheet materials most often is caused by variability in the cooling rates resulting in localized variations in the index of refraction for the transparent sheet material. Heat distortion patterns are often not easily separated from ripple patterns since heat distortion often orients with ripples. For this reason, these ripple and distortion are typically evaluated together.

Distortion is mathematically defined as the rate of change of the angular deviation of a light beam across a transparent sheet (or film). Distortion in a transparent sheet may be determined by mapping, at a plurality of locations on the transparent sheet, the angular deviation of light beams as they are transmitted from the light source through the transparency to the observer.

Angular deviation is different than the normal lateral displacement (lateral shifting) of the light beam as it passes through the transparent sheet material. Whenever a beam of light passes through the transparent sheet material at an angle other than perpendicular to the face of the sheet, lateral displacement of the beam by a relatively small and constant amount results. However, when a beam of light passes through the transparent sheet at the same angle, but where the faces of the transparency are non-parallel, both lateral displacement and angular deviation result. While lateral displacement is generally insignificant in automotive windshield applications and the like, the angular deviation and distortion causes the distance between the real location of the object and its apparent (angular deviation) position to increase as the range of the object from the observer increases. Consequently, a method of quantifying the angular deviation and the distortion in a transparent material to ascertain the severity of the distortion is beneficial in quantifying the acceptable limits of ripple and distortion for the intended application.

Distortion is typically analyzed based on the non-linear mapping of objects viewed through the transparent sheet, such that the actual physical position of an object does not linearly correspond to its apparent location as seen through the glass or other transparent sheet. In the case of a perfect non-distorting transparent sheet, a square grid object would be reproduced as an identical square grid in the image plane. Where there are wedge variations, curvature variations, optical index defects, or the like, in the transparent sheet, the square grid will be reproduced in a distorted form in the image plane.

The existing methods and systems for detecting and measuring distortion are difficult to use, time consuming, and unreliable. Many of the test systems involve some form of manual inspection procedure. A conventional inspection procedure involves a visual inspection from a distant position of a stripe pattern or grid pattern through the transparent sheet. An inspector in viewing the pattern can visually determine the optical quality. The zone with the largest defect is located and a measurement of the distortion is made where the distortion is the greatest. Reference transparent sheets may be used to arbitrarily assign a value to the test transparency. However, real quantitative standardization cannot be obtained and differences among inspectors prevent uniform inspection quality.

SUMMARY OF THE INVENTION

A method and apparatus for quantitatively measuring a level of ripple and distortion in a transparent sheet material is provided. The method comprises projecting an image of a transparent sheet material onto a screen; digitally capturing an image of at least a portion of the shadowgraph; generating parameter signals from the digital image, wherein the parameter signals comprise $\sigma_y$, $\sigma_{pxp}$, $f_{1''}$, and $f_{0.3''}$; and quantitatively assigning a value to the level of ripple and distortion present in the transparent sheet material based on the parameter signals.

The apparatus for measuring ripple and distortion in a transparent product comprises a light source positioned to direct light beams onto a screen; a frame assembly intermediate the light source and the screen, wherein the frame assembly is adapted to hold a transparent sheet material and is mounted at about a combined angle of forty five degrees with respect to the ground and the screen; an image capture device mounted to the frame assembly and focused at a plane defined by the screen; and an image analysis system coupled to the image capture device and adapted to receive and process image signals from the image capture device.

These and other features will be apparent from the following brief description of the drawings, detailed description, and attached drawings.

BRIEF DESCRIPTION OF THE DRAWINGS

Referring now to the following Figures, in which:

FIG. 6 is a table depicting a ripple and distortion model developed using parameter signals obtained from an image digitally captured using the apparatus of FIG. 1.

DETAILED DESCRIPTION OF THE INVENTION

A process and apparatus for quantitatively assessing ripple and distortion in a transparent material generally includes digital capture of a shadowgraph generated by passing light through the transparent material. The digital image created by the shadowgraph is then analyzed and assigned quantifiable metrics for describing the amount of ripple and distortion in the transparent material. The transparent material is preferably an extruded transparent plastic sheet or a transparent film. Advantageously, the process and apparatus may be employed as the sheet material is extruded, thereby providing real time feedback on the amount of ripple and distortion present.

Figure 1:
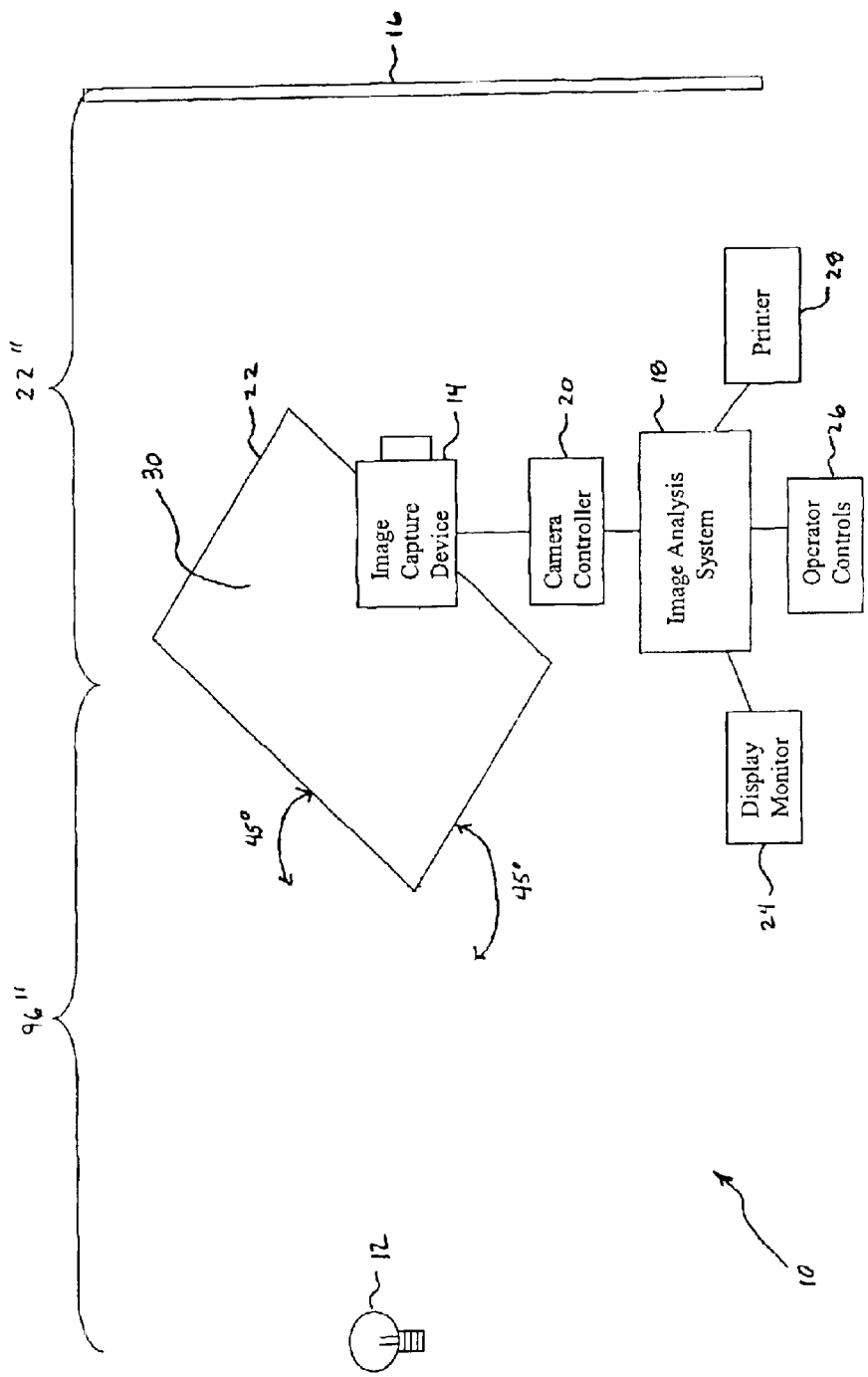
FIG. 1 schematically illustrates an apparatus for measuring ripple and distortion in a transparent substrate.
Figure 2:
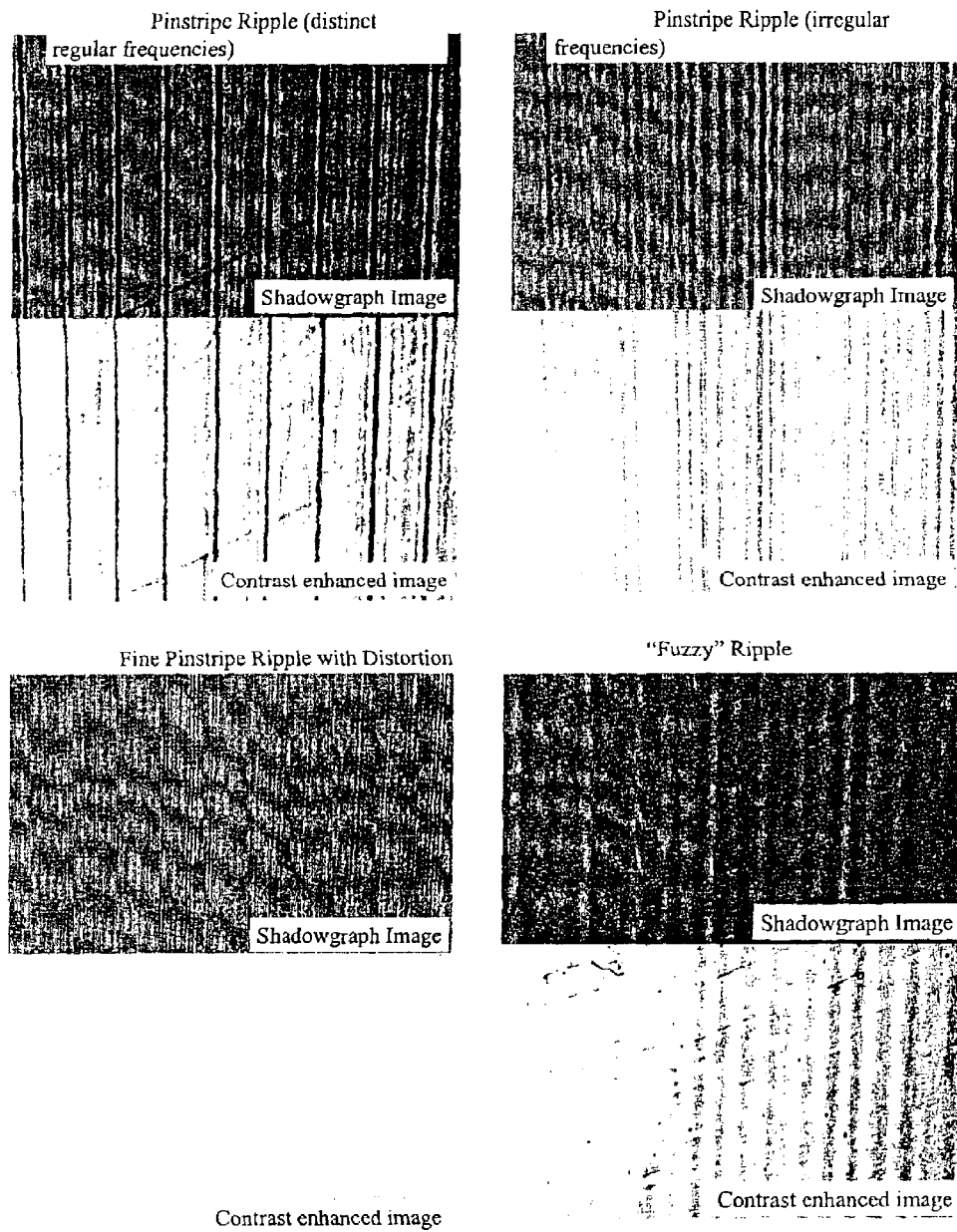
FIGS. 2 and 3 pictorially illustrate shadowgraph images and contrast-enhanced images for some of the various ripple and distortion optical patterns found in a transparent sheet material.
Figure 3:
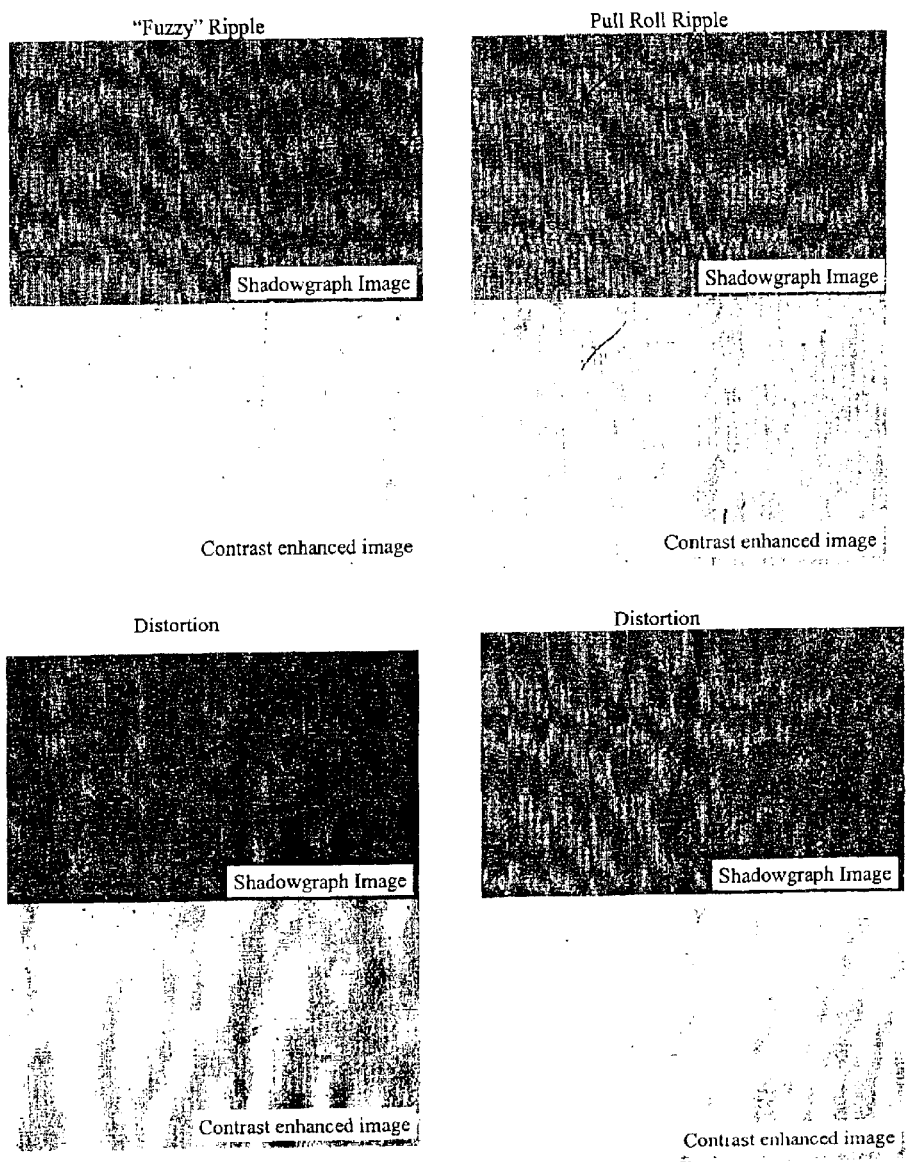

Referring now to FIG. 1, the apparatus 10 for measuring ripple and distortion includes a light source 12, an image capture device 14, a screen 16, and an image analysis system 18. Light beams are directed from the light source 12 through a transparent material 30 to project a shadowgraph onto the screen 16. FIGS. 2 and 3 pictorially illustrate shadowgraphs showing various types of ripple and distortion optical patterns found in transparent sheet materials. Preferably, the light beams are emitted from a xenon arc light source. During projection of the light beams through the transparent material 30, other light sources that may interfere with the light beams are preferably dimmed or turned off, e.g., room lights.

The image capture device 14 is coupled to a camera controller 20. The image capture device 14 is mounted to a frame assembly 22 and is focused onto the screen 16. A digital camera can be employed as the image capture device 14, such as the Olympus D620-L digital camera. Other suitable image capture devices include, but are not limited to, a video camera, a charge couple device (CCD) camera, a laser line-by-line scanning system, and the like. The image capture device 14 captures an image, i.e., a shadowgraph, displayed on the screen and transmits the image signals to the camera controller 20.

The transparent sheet material 30 is positioned in the frame assembly 22. In a preferred embodiment, the transparent sheet material 30 is positioned about 8 feet away from the light source 12. Preferably, the frame assembly 22 is about 24 inches by 24 inches and is adapted to hold the transparent sheet material 30 in a planar configuration. The frame assembly 22 is oriented such that the transparent sheet material 30 lies about at a combined 45-degree angle with respect to the ground 32 and the horizon, although the angle can vary as needed or desired. In this manner, the centermost point, i.e., midpoint, of the transparent material 30 is preferably about 8 feet away from the light source 12 and about 22 inches from the screen 16.

The image analysis system 18 is coupled to the camera controller 20 and receives the image signals from the image capture device 14 via the camera controller 20. Although in this particular embodiment, the image analysis system 18 receives the image signals from the image capture device 14, image signals could already be stored in memory and could be transmitted to the image analysis system 18 in response to a request signal from the image analysis system 18. The image analysis system 18 includes a central processing unit and memory, which has a program stored in a manner well known in the art which causes operation of the process for measuring optical distortion in a transparent material. The image analysis system 18 is coupled to an operator control 26 such as a keyboard or mouse, which enables an operator to interact with the image analysis system 18, i.e., to input commands. Preferably, the image analysis system 18 is further coupled to a printer 28 and a display monitor 24. Thus, the captured image can be transmitted to the display monitor 24 and/or printed.

The transparent sheet material 30 may comprise individual sheets, laminated sheets, or may comprise a continuous web of an individual or laminated sheet passing through the frame. Preferably, the transparent sheet material 30 comprises a continuous web as it is being extruded from an extruder apparatus (not shown) and into the frame assembly 22. The thickness of the transparent sheet is preferably about 1.5 inches to about 0.030 inches. The thickness of a transparent film material is preferably about 0.030 inches to about 0.001 inches.

Figure 4:
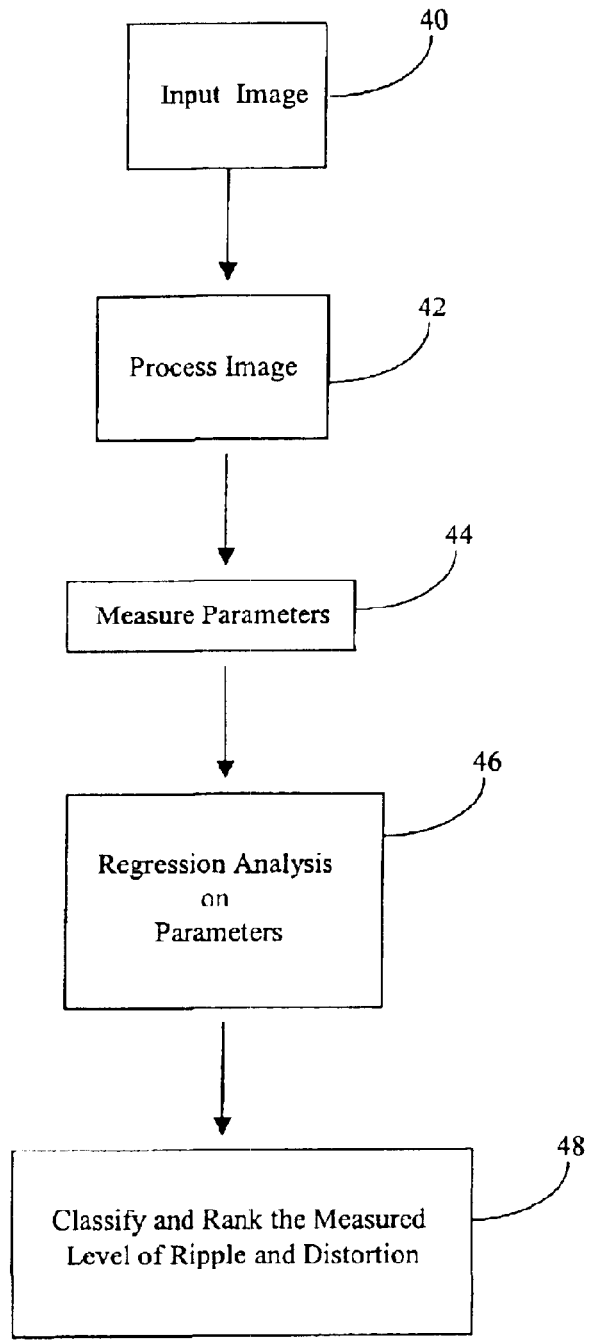
FIG. 4 illustrates a process flow measuring ripple and distortion in a transparent substrate.

FIG. 4 illustrates a flow chart of a process for measuring optical distortion in a transparent material programmed in the memory of the image analysis system. The image signals to be analyzed are input 40 from the image capture device 14, which comprises an image of the shadowgraph projected onto the screen 16.

For illustrative purposes, the image capture device 14, e.g., the Olympus digital camera, is operated at full zoom and digitally captures a 15 inch by 14 inch area of the image projected onto the screen 16. The camera is focused on a center point of the 15-inch by 14-inch image area. Focusing the camera can be achieved by temporarily replacing the screen with a white poster board. A focal point, e.g., a black one-inch square, is placed on the poster board at about the center of the image area upon which the camera is then focused. The poster board is subsequently replaced with the screen.

In another embodiment, the image capture device 14 is a line camera system. A suitable laser based line camera system is a LASOR 2fl scanning system commercially available from Lasor/Systronics in Norcross, Ga. Suitable CCD based line cameras are available from Nanosystems GmbH & Co. of Bochum Germany.

Prior to quantitatively measuring ripple and distortion in a sample transparent sheet material, an image of the blank screen (no sample present) is digitally captured and stored in the image analysis system 18. The digitally captured image signals of the blank screen 16 will later be subtracted during the image analysis to account for optical contributions caused by the screen 16.

Next, the input image signals 40 are processed 42 in the image analysis system 18. The input image signals comprise a digital image of the shadowgraph, e.g., a digital image of the 15-inch by 14-inch image area. In one embodiment, a slice of the digital image that cuts across a ripple pattern (i.e., in the machine direction) is digitally captured and transferred to the image analysis system 18. A Fourier transform analysis of the gray scale data is then analyzed to determine those wavelengths that contribute the greatest to the variability in gray scale. Alternatively, filters may be applied to the entire image area to highlight certain aspects of the image, such as, for example, vertical coherence. The histogram of these captured pixel intensities can then be analyzed in order to quantify the variability in gray scale.

Parameter signals are then measured 44 from the processed image, i.e., shadowgraph. The parameters utilized for quantitatively determining ripple and distortion quality include the terms $\sigma_{pxp}$, $\sigma_v$, $f_{1"}$ and $f_{0.3"}$. The term $\sigma_{pxp}$ represents the standard deviation of the pixel-to-pixel difference over the full area of the captured image, i.e., 15 inches by 14 inches. As such, the $\sigma_{pxp}$ parameter captures the edge contrast and high frequency contributions of the image. For example, if 1.2 million pixels are used within the 15 inch by 14 inch image area, a 500-pixel threshold on the 8-bit intensity histogram is preferably used to exclude scratches and other localized defects.

The $\sigma_v$ parameter represents the standard deviation for a defined area, e.g., a 7-inch by 14-inch area, after the image has been averaged in the vertical direction, wherein the vertical direction is parallel with the primary ripple orientation. A filter is performed to highlight the ripple coherence and low frequency amplitude in the machine direction. The filter is programmed to select every $20^{th}$ pixel in the vertical (cross web) direction (out of the 1024 pixels representing 14 inches) then replace each pixel with the average of 4 pixels directly above and below the given pixel (nine point running average). After the filter is applied, a histogram of the pixel intensities is generated. The parameter $\sigma_v$ is the standard deviation of the histogram for intensities that exceed a 100 pixel threshold.

The $f_{1"}$ and $f_{0.3"}$ parameters represent the summed contribution of wavelengths between about 1.7 inches to about 0.5 inches, and about 0.2 inches to about 0.5 inches, respectively. These parameters are used based on the Fourier transform analysis of the intensity variation of a line about 12 inches by about 0.02 inches (1024 pixels by 1 pixel) in the machine direction. The magnitudes of the Fourier transform frequencies are normalized by the total magnitude to make the frequency metrics independent of the overall standard deviation, which are captured in the $\sigma_{pxp}$ and $\sigma_v$ parameters A regression analysis 46 is then used to determine a function to best fit the set of data observations. The data observations include analysis of samples of transparent sheet material that represent different levels of ripple and distortion. The levels of ripple and distortion for each sample are ranked by inspectors to allow interpretation of the various parameters relative to the overall optical quality. The regression analysis provides a model to fit the data observations.

The model results are then used to rank and classify the measured ripple and distortion 48. The particular level of acceptable ripple and distortion can vary and may depend on a number of factors, such as type of materials, material thickness, the desired quality level and the acceptable level of distortion. Each manufacturer can set its own standards as needed and desired.

The following examples are presented for illustrative purposes only, and are not intended to limit the scope of the invention.

EXAMPLE 1

In this example, a model was generated from forty-eight transparent polycarbonate sheet samples as shown in Tables 1 and 2.

TABLE 1

| Ex. | Gauge (mil) | Worm Drive | Roll Ratio | $\sigma_{pxp}$ | $\sigma_v$ | $f_{1"}$ | $f_{0.3"}$ | Avg. Rank | AA scale | Model |
|---|---|---|---|---|---|---|---|---|---|---|
| 1 | 125 | — | — | 3.02 | 1.66 | 0.093 | 0.151 | 3.88 | 6.12 | 5.08 |
| 2 | 110 | — | — | 3.22 | 1.69 | 0.095 | 0.156 | 6.47 | 7.15 | 5.49 |
| 3 | 110 | — | — | 3.23 | 1.72 | 0.104 | 0.138 | 4.82 | 6.49 | 5.60 |
| 4 | 236 | — | — | 3.46 | 2.04 | 0.105 | 0.153 | 8.29 | 7.72 | 6.83 |
| 5 | 118 | — | — | 3.38 | 2.24 | 0.101 | 0.159 | 5.18 | 6.64 | 7.17 |
| 6 | 236 | — | — | 3.85 | 2.40 | 0.101 | 0.135 | 7.41 | 7.44 | 7.29 |
| 7 | 118 | — | — | 4.22 | 2.76 | 0.086 | 0.142 | 13.59 | 9.36 | 7.65 |
| 8 | 100 | — | — | 2.96 | 1.91 | 0.129 | 0.190 | 8.53 | 7.81 | 8.04 |
| 9 | 110 | — | — | 4.19 | 2.47 | 0.105 | 0.142 | 16.29 | 10.02 | 8.05 |
| 10 | 197 | — | — | 4.40 | 2.29 | 0.127 | 0.127 | 12.41 | 9.01 | 8.37 |
| 11 | 80 | — | — | 2.99 | 2.57 | 0.192 | 0.187 | 21.47 | 11.53 | 10.14 |
| 12 | 375 | — | — | 3.44 | 3.04 | 0.167 | 0.159 | 19.65 | 11.00 | 10.83 |
| 13 | 375 | — | — | 3.77 | 3.04 | 0.187 | 0.154 | 20.47 | 11.19 | 10.99 |
| 14 | 177 | — | — | 7.57 | 3.58 | 0.093 | 0.092 | 21.06 | 11.39 | 11.16 |
| 15 | 236 | — | — | 4.10 | 3.35 | 0.161 | 0.134 | 17.94 | 10.54 | 11.32 |
| 16 | 236 | — | — | 5.95 | 3.32 | 0.128 | 0.114 | 17.06 | 10.23 | 11.45 |
| 17 | 118 | — | — | 3.74 | 3.47 | 0.191 | 0.148 | 22.88 | 11.97 | 11.69 |
| 18 | 236 | — | — | 4.12 | 3.32 | 0.145 | 0.170 | 17.41 | 10.35 | 11.84 |
| 19 | 500 | — | — | 3.60 | 3.83 | 0.167 | 0.164 | 23.82 | 12.24 | 12.72 |
| 20 | 93 | — | — | 3.86 | 4.95 | 0.150 | 0.259 | 28.29 | 19.49 | 17.29 |
| 21 | 150 | new | 1 | 3.19 | 1.64 | 0.078 | 0.152 | 1.47 | 5.00 | 4.29 |
| 22 | 150 | new | 1 | 3.08 | 1.71 | 0.079 | 0.162 | 4.24 | 6.25 | 4.63 |
| 23 | 93 | new | 0.9 | 3.43 | 1.94 | 0.094 | 0.159 | 8.41 | 7.78 | 6.19 |
| 24 | 93 | new | 1 | 3.85 | 2.42 | 0.097 | 0.177 | 15.00 | 9.70 | 8.13 |
| 25 | 150 | old | 1 | 3.43 | 2.58 | 0.133 | 0.135 | 16.88 | 10.18 | 8.61 |
| 26 | 93 | new | 1 | 4.60 | 2.42 | 0.105 | 0.162 | 12.59 | 9.05 | 8.70 |
| 27 | 150 | old | 0.9 | 3.77 | 4.35 | 0.211 | 0.171 | 24.06 | 12.33 | 13.85 |
| 28 | 150 | old | 1.1 | 4.00 | 5.04 | 0.175 | 0.231 | 26.94 | 17.51 | 17.16 |
| 29 | 93 | new | 1.1 | 7.25 | 7.62 | 0.055 | 0.310 | 28.47 | 19.77 | 21.98 |
| 30 | 93 | old | 1.1 | 7.11 | 7.17 | 0.089 | 0.379 | 30.00 | 26.08 | 24.90 |

TABLE 2

| Example | Gauge | Rating | $\sigma_{pxp}$ | $\sigma_v$ | $f_{1''}$ | $f_{0.3''}$ | Nominal rank | AA scale | Model |
|---|---|---|---|---|---|---|---|---|---|
| 31 | 118 | 3.5 | 3.45 | 2.11 | 0.129 | 0.164 | 5 | 6 | 8.22 |
| 32 | 80 | — | 3.41 | 2.88 | 0.102 | 0.234 | 10 | 8 | 10.37 |
| 33 | 375 | 3.5 | 4.89 | 4.35 | 0.180 | 0.139 | 25 | 12 | 14.25 |
| 34 | 500 | 3.5 | 9.13 | 6.40 | 0.182 | 0.115 | 28 | 22 | 21.24 |
| 35 | 500 | 4.5 | 3.71 | 8.00 | 0.206 | 0.175 | 29 | 23 | 21.65 |
| 36 | 250 | — | 3.95 | 2.05 | 0.086 | 0.155 | 4 | 7 | 6.25 |
| 37 | 125 | — | 3.85 | 2.29 | 0.106 | 0.131 | 4 | 7 | 7.22 |
| 38 | 115 | — | 3.47 | 1.92 | 0.133 | 0.180 | 4 | 7 | 8.34 |
| 39 | 211 | — | 3.44 | 2.71 | 0.239 | 0.164 | 15 | 10 | 9.16 |
| 40 | 170 | — | 3.44 | 2.68 | 0.129 | 0.168 | 4 | 7 | 9.49 |
| 41 | — | — | 2.51 | 0.96 | 0.048 | 0.133 | 0 | 0 | -0.38 |
| 42 | — | — | 2.50 | 0.82 | 0.056 | 0.132 | 0 | 0 | -0.03 |
| 43 | — | — | 2.51 | 0.86 | 0.050 | 0.152 | 0 | 0 | 0.03 |
| 44 | — | — | 2.50 | 0.89 | 0.056 | 0.128 | 0 | 0 | 0.04 |
| 45 | — | — | 2.42 | 1.47 | 0.052 | 0.106 | 0 | 0 | 0.31 |
| 46 | — | — | 2.50 | 0.99 | 0.068 | 0.122 | 0 | 0 | 0.98 |
| 47 | — | — | 2.52 | 1.19 | 0.064 | 0.136 | 0 | 0 | 1.49 |
| 48 | — | — | 2.33 | 1.17 | 0.076 | 0.128 | 0 | 0 | 1.92 |

Examples 1 through 20 included various transparent sheet materials obtained from production runs. Examples 21–30 included various transparent sheet materials produced from a production line before and after a worm drive was replaced. In Examples 21–30, a roll ratio was also varied. The roll ratio is defined as the relative speed of a first roller compared to a second roller as the sheet is extruded between the two rollers. The roll ratio was varied from a nominal roll ratio (1.0) to +10% (1.1) and −10% (0.9). Shadowgraphs of the transparent sheet materials were digitally captured using the apparatus described in FIG. 1. The shadowgraphs were printed for each example and visually ranked by seventeen different inspectors using a scale of 1 to 30, wherein 1 represented high optical quality (lowest amount of ripple and distortion present) and 30 represented low optical quality (highest amount of ripple and distortion present). The average rank and standard deviation were then determined for each shadowgraph. The results of the visual ranking by the inspectors indicate that either the differences between shadowgraphs were qualitatively indistinguishable, or that individual inspectors were weighing different aspects of the image for their qualitative analysis in deciding which shadowgraph has the higher ripple and distortion. Moreover, since the increment in difference by forced ranking is not captured (i.e., the difference in quality between the 29$^{th}$ ranked and the 30$^{th}$ ranked samples may be different from the qualitative difference in quality may be different between the 14$^{th}$ and 15$^{th}$ ranked samples), quality was determined by using both the average rank and the standard deviation of the rank.

Qualitatively, it was determined upon visual inspection of the shadowgraphs that the lower the amplitude of waviness, wherein the amplitude represents the brightness of the bright bands compared to the darkness of the dark bands present in the shadowgraph. Thus, low amplitude is indicative of a lack of contrast or low contrast between the light and dark areas. Similarly, it was determined that a low edge contrast is generally preferred, wherein the edge contrast represents the transition form the dark to the light area or vice versa. The wavelength or periodicity of oscillations between light and dark bands has been determined to affect ripple quality. Wavelengths less than or equal to about 0.08 inches (at the limit of visual detection) and wavelengths greater than or equal to 3 inches are preferred in terms of visual optical quality. Wavelengths from about 0.25 inches to about 2 inches were least preferred. For cross web coherence, it is preferred that the ripple bands fade in and out as opposed to a constant cross web line.

Examples 31 through 35 included polycarbonate samples having known quality rating standards. The ratings were determined on a scale of 1 to 5, wherein a rating of 1 indicates superior optical quality relative to a rating of 5.0. Examples 36 through 40 included commercially obtained samples of polycarbonate sheet material. Examples 31 through 40 were rated relative to the forced ranked samples of Examples 1 through 30 and given the nominal rankings shown in Table 2.

Examples 41 through 48 included data obtained from shadowgraphs of the blank screen.

Figure 5:
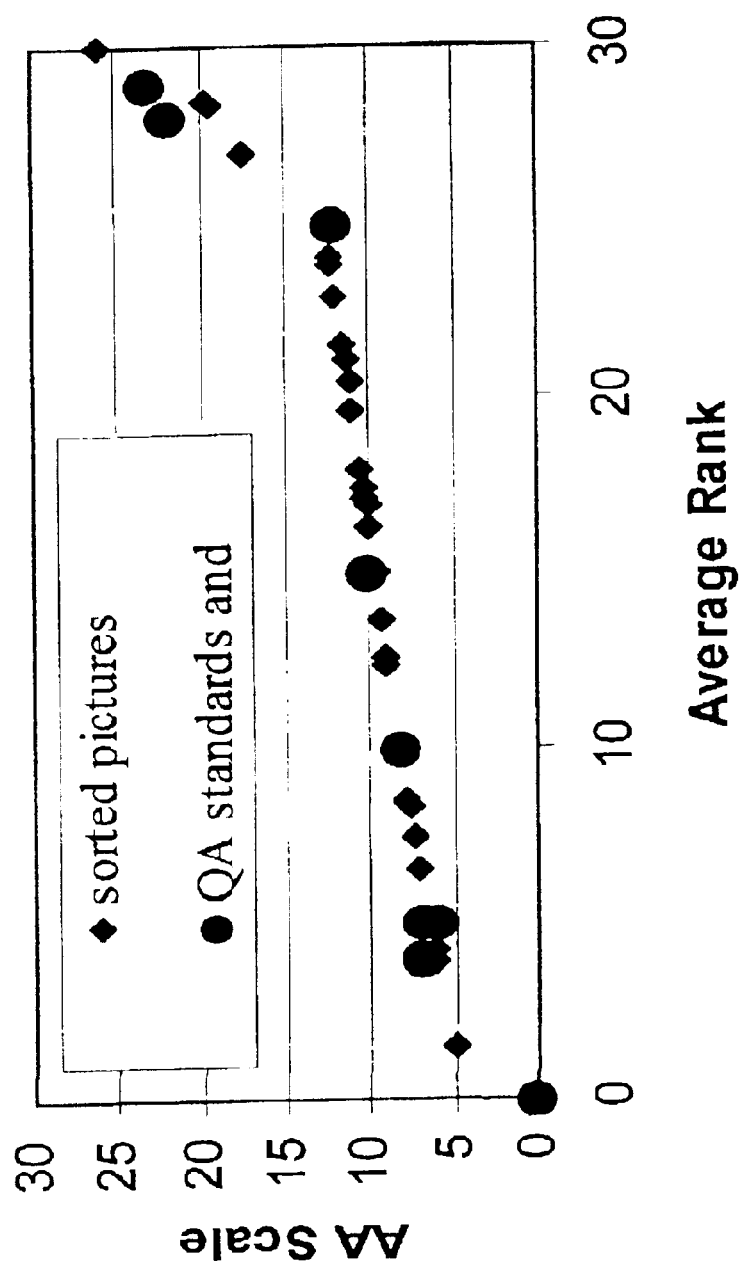
FIG. 5 graphically illustrates average rank as a function of AA scale.

The average rank ordering (Examples 1 through 30) and nominal rank ordering (Examples 31 through 40) were then converted into an absolute scale (AA scale) using a scale from 1 to 5, wherein 5 represents the best ranked example and 1 represents the worst ranked example. The value of the next best sample based on the qualitative analysis described above is calculated as the difference between the average (or nominal) ranking of the current and previous samples divided by the standard deviation in the ranking of the current sample. The digital images of the blank screen (Examples 41–48) were assigned a ranking and AA scale of 0. FIG. 5 graphically illustrates the average rank order as a function of the AA scale.

A model using regression analysis was then generated by the image analysis system using the parameters previously described and fit to the AA scale in accordance with the following mathematical formula (I):

$$\text{Model} = -12.2 + 2.10\,\sigma_v + 0.761\,\sigma_{pxp} + 115\,f_{1''} - 320(f_{1''})^2 + 23.5\,f_{0.3''} \quad (I)$$

As shown in FIG. 6, the model produced a proportion of variation ($R^2$) of 95.3%, an adjusted $R^2$ of 94.8% with a model standard deviation of 1.38.

The contribution of the individual parameters is shown in Table 3. The minimum and maximum values are shown. The results indicate that $\sigma_v$ has about three times the impact on the ripple and distortion model relative to parameters, $\sigma_{pxp}$, $f_{1''}$, and $f_{0.3''}$

TABLE 3

|  | $\sigma_{pxp}$ | $\sigma_v$ | $f_{1"}$ | $f_{0.3"}$ |
| --- | --- | --- | --- | --- |
| Minimum | 2.33 | 0.82 | 0.05 | 0.09 |
| Maximum | 9.13 | 8.00 | 0.24 | 0.38 |
| Minimum model contribution | 1.77 | 1.73 | 4.76 | 2.17 |
| Maximum model contribution | 6.95 | 16.79 | 9.19 | 8.90 |
| Model range | 5.18 | 15.06 | 4.43 | 6.73 |

Advantageously, the model provides a means for quantifying the ripple and distortion levels present in a transparent sheet material. The model and apparatus is relatively simple and can be utilized to provide a real time quantitative analysis of the transparent sheet material as it is extruded. Eliminating the ambiguity associated with qualitative inspection methods is a significant commercial advantage leading to improved and more consistent quality. Moreover, use of the present model and apparatus provides manufacturers with a ripple and distortion specification that can be tailored to its customer's requirements.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for quantitatively measuring a level of ripple and distortion in a transparent sheet material, the method comprising:

projecting projected image of the transparent sheet material onto a screen, digitally capturing digital image of at least a portion of the projected image and generating parameter signals from the digital image, wherein the parameter signals comprise $\sigma_v$, $\sigma_{pxp}$, $f_{1"}$, and $f_{0.3"}$ wherein $\sigma_v$ represents a standard deviation for a defined area, $\sigma_{pxp}$ represents a standard deviation of a pixel-to-pixel difference over a full area of the digital image, $f_{1"}$ represents a summed contribution of wavelengths of about 1.7 inches to about 0.5 inches, and $f_{0.3"}$ represents a summed contribution of wavelengths of about 0.2 inches to about 0.5 inches; and quantitatively assigning a value to the level of ripple and distortion present in the transparent sheet material.

2. The method of claim 1, wherein the projected image is a shadowgraph.

3. The method of claim 1, further comprising digitally capturing an image of a blank screen, and adjusting the parameter signals to account for optical contributions from the blank screen.

4. The method of claim 1, further comprising inputting the parameter signals into a model according to formula (I):

$$\text{Ripple/Distortion} = -12.2 + 2.10\ \sigma_v + 0.761\ \sigma_{pxp} + 115\ f_{1"} + -320(f_{1"})^2 + 23.5\ f_{0.3"} \quad (I).$$

5. The method of claim 1, wherein polynomial coefficients for the parameter signals $\sigma_v$, $\sigma_{pxp}$, $f_{1"}$, and $f_{0.3"}$ are based on a regression analysis of data obtained from other transparent sheet materials.

6. The method of claim 1, wherein the transparent sheet material is a continuous web.

7. The method of claim 1, further comprising means for filtering the image signals.

8. An apparatus for measuring ripple and distortion patterns in a transparent product, the apparatus comprising, a light source positioned to direct light beams onto a screen;

a frame assembly intermediate to the light source and the screen, wherein the frame assembly is adapted to hold a transparent sheet material and is mounted at about a combined angle of about forty five degrees with respect a first plane defined by a light line connecting the light source to a center of the screen and a vertical line through the center of the screen, and at a combined angle of about forty five degrees with respect to a second plane defined by the light line and a horizontal line through the center of the screen, wherein the light line, vertical line, and horizontal line are all perpendicular to one another with respect to a ground and a horizon;

an image capture device mounted to the frame assembly and focused at a plane defined by the screen; and an image analysis system coupled to the image capture device and adapted to receive and process image signals from the image capture device;

wherein the image analysis system comprises means for determining parameter signals from the image signals, and wherein the parameter signals comprise $\sigma_v$, $\sigma_{pxp}$, $f_{1"}$, and $f_{0.3"}$, wherein $\sigma_v$ represents a standard deviation for a defined area, $\sigma_{pxp}$ represents a standard deviation of a pixel-to-pixel difference over a full area of the digital image, $f_{1"}$ represents a summed contribution of wavelengths of about 1.7 inches to about 0.5 inches, and $f_{0.3"}$ represents a summed contribution of wavelengths of about 0.2 inches to about 0.5 inches.

9. The apparatus of claim 8, wherein the light source is positioned about eight feet away from a midpoint of the transparent sheet material in the frame assembly, and the screen is disposed about twenty-two inches from the midpoint of the transparent sheet material such that a light beam from the light source passes though the transparent sheet material and projects a shadowgraph onto the screen.

10. The apparatus of claim 8, wherein the light source comprises a xenon light.

11. The apparatus of claim 8, wherein the image capture device is selected from the group consisting of a digital camera, a CCD camera, and a video camera.

12. The apparatus of claim 8, wherein the frame assembly is adapted to receive a continuous web of the transparent sheet material.

13. The apparatus of claim 8, wherein the image analysis system comprises means for determining parameter signals from the image signals.

14. The apparatus of claim 8, further comprising a model according to formula (I):

$$\text{Ripple/Distortion} = -12.2 + 2.10\ \sigma_v + 0.761\ \sigma_{pxp} + 115\ f_{1"} + -320(f_{1"})^2 + 23.5\ f_{0.3"} \quad (I).$$

15. The apparatus of claim 8, wherein polynomial coefficients for the parameter signals $\sigma_v$, $\sigma_{pxp}$, $f_{1"}$, and $f_{0.3"}$ are based on a regression analysis of data obtained from other transparent products.

16. The apparatus of claim 8, wherein the transparent product is a continuous web.

17. The apparatus a claim 8, further comprising means for filtering the image signals.

* * * * *